United States Patent [19]
Ho

[11] Patent Number: 5,667,964
[45] Date of Patent: Sep. 16, 1997

[54] RAPID, DIRECT, AND QUALITATIVE METHOD FOR THE DETERMINATION OF THE NUMBER OF HIV-1-INFECTED PATIENT CELLS EMPLOYING REACTIVE OXYGEN INTERMEDIATE GENERATORS

[75] Inventor: John Lap Ho, New York, N.Y.

[73] Assignee: Cornell Research Foundation, Inc., Ithaca, N.Y.

[21] Appl. No.: 331,218

[22] Filed: Oct. 28, 1994

[51] Int. Cl.$^6$ .............................. C12Q 1/70; C12Q 1/00
[52] U.S. Cl. ................................... 435/5; 435/4
[58] Field of Search ............... 435/4, 5, 71, 72, 435/721, 724, 235.1

[56] References Cited

U.S. PATENT DOCUMENTS

| | | |
|---|---|---|
| 4,404,280 | 9/1983 | Gillis . |
| 4,411,992 | 10/1983 | Gillis . |
| 4,683,199 | 7/1987 | Palladino . |
| 4,785,077 | 11/1988 | Kornbluth et al. . |
| 4,886,742 | 12/1989 | Kortright et al. ............ 435/5 |
| 5,256,534 | 10/1993 | Butera et al. ............... 435/5 |

OTHER PUBLICATIONS

Folks, et al., "Cytokine Induced Expression of HIV–1 in a Chronically Infected Promonocyte Line," *Science*, 238:801–802 (1987).

Castro, et al., "Optimal Conditions for Recovery of the Human Immunodeficiency Virus from Peripheral Blood Mononuclear Cells," *J. Clin. Microbiol.*, 26:2371–2376 (1988).

Folks, et al., "Characterization of a Promonocyte Clone Chronically Infected With HIV and Inducible By 13–Phorbol 12–Myristate Acetate," *J. Immunol*, 140:1117–1122 (1988).

Ho, et al., "Diminished Activity of Protein Kinase C in Tetanus Toxin–Treated Macrophages and in the Spinal Cord of Mice Manifesting Generalized Tetanus Intoxication," *J. Infect. Dis.*, 157:925–933 (1988).

Jackson, et al., "Rapid and Sensiive Viral Culture Method for Human Immunodeficiency Virus Type 1," *J. Clin. Microbiol.*, 26:1416–18 (1988).

(List continued on next page.)

*Primary Examiner*—Christine M. Nucker
*Assistant Examiner*—Jeffrey S. Parkin
*Attorney, Agent, or Firm*—Nixon, Hargrave, Devans & Doyle

[57] ABSTRACT

The ability to monitor the progression of human immunodeficiency virus (HIV) infection in patients is paramount to the study of HIV transmission, in predicting the onset and advancement of disease, and evaluating the clinical efficacy of therapeutics. Present methods available to the clinician for the study of HIV pathogenesis employ surrogate markers. Surrogate markers are biological indicators that tend to reflect, to varying extent, the gradual progression of the asymptomatic state to the development of acquired immune deficiency syndrome (AIDS). The most commonly used markers are $CD4^+$ lymphocyte counts and HIV p24 antigen production. The use of markers to evaluate disease progression suffers from a number of limitations. No known marker consistently reflects disease progression in all patients and stages of disease. Moreover, an effective marker must rapidly reflect the changes associated with antiviral therapy. Accordingly, there still exists in the field a need for a rapid and direct technique for assessing the viral load of an HIV-infected patient. The present invention discloses a rapid method for qualitatively determining the number of HIV-1-infected patient cells in a sample. Patient cells are subjected to direct stimulation with reactive oxygen intermediate generator(s), in the absence of co-culture with donor cells, and the quantity of p24 antigen produced from said stimulation ascertained. These values are compared to those values obtained from HIV-1 chronically infected cell lines of known proviral copy number (e.g., ACH-2 and U1.1) and the number of infected patient cells determined. This method provides a facile, rapid, and direct method for the assessment of viral load.

24 Claims, 4 Drawing Sheets

OTHER PUBLICATIONS

Coombs, et al., "Plasma Viremia in Human Immunodeficiency Virus Infection," *N. Engl. J. Med.*, 321:1626–1631 (1989).

Duh, et al., "Tumor Necrosis Factor–α Activates Human Immuno–deficiency Virus Type–1 Through Induction of Nuclear Factor Binding to the NF–kB Sites in the Long Terminal Repeat," *Proc. Natl. Acad. Sci. USA*, 86:5974–5978 (1989).

Harry, et al. "Antigen Detection for Human Immunodeficiency Virus," *Clin. Microbiol. Rev.* 2:241–260 (1989).

Ho, et al., "Quantitation of Human Immunodeficiency Virus Type I in the Blood of Infected Persons," *N. Engl. J. Med.*, 321:1621–1625 (1989).

Osborn, et al. "Tumor Necrosis Factor–α and Interleukin–1 Stimulate the Human Immunodeficiency Virus Enhancer by Activation of the Nuclear Factor kB," *Proc. Natl. Acad. Sci. USA*, 86:2336–2340 (1989).

Poli, et al., "Interferon–α but Not AZT Suppresses HIV Expression In Chronically Infected Cell Lines," *Science*, 244:575–577 (1989).

Schochetman, et al., "Serodiagnosis of Infection With the AIDS Virus and Other Human Retroviruses," *Annu. Rev. Microbiol.*, 43:629–659 (1989).

Jackson, et al., "Human Immunodeficiency Virus Type 1 Detected in All Seropositive Symptomatic and Asymptomatic Individuals," *J. Clin. Microbiol.*, 28:16–19 (1990).

Kinter, et al., "Direct and Cytokine–Mediated Activation of Protein Kinase C Induces Immunodeficiency Virus Expression In Chronically Infected Promonocytic Cells," *J. Virol.*, 64:4306–4312 (1990).

McSharry, et al., "Detection and Quantitation of Human Immunodeficiency Virus–Infected Peripheral Blood Mononuclear Cells by Flow Cytometry," *J. Clin. Microbiol.*, 28:724–733 (1990).

Moss, A.R., "Laboratory Markers as Potential Surrogates for Clinical Outcomes.," *J. Acquired Immune Defic. Syndr.*, 3(Suppl. 2):S69–S71 (1990).

Poli, et al. "Tumor Necrosis Factor–α Functions in an Autocrine Manner in the Induction of Human Immunodeficiency Virus Expression," *Proc. Natl. Acad. Sci. USA*, 87:782–785 (1990).

Schreck, et al., "Reactive Oxygen Intermediates As Apparently Widely Used Messengers In the Activation of the NF–kB Transcription Factor and HIV–1," *Embo. J.*, 10:2247–2258 (1991).

Alimenti, et al., "Diagnois of Vertical Human Immunodeficiency Virus Type 1 Infection By Whole Blood Culture," *J. Infect. Dis.*, 166:1146–1148 (1992).

Bylung, et al., "Review of Testing For Human Immunodeficiency Virus," *Laboratory Immunology II. Clin. Lab. Med.*, 12:305–333 (1992).

Mufson, et al., "Phorbol Ester Reduces Constitutive Nuclear NF–kB and Inhibits HIV–1 Production in Mature Human Monocytic Cells," *J. Leukocyte Biol.*, 52:637–644 (1992).

Poli, et al., "The Effect of Cytokines and Pharmacologic Agents On Chronic HIV Infection," *AIDS Res. Hum. Retroviruses*, 8:191–197 (1992).

Schreck, et al. "Antioxidants Selectively Suppress Activation of NF–kB by Human T Cell Leukemia Virus Type I Tax Protein," *J. Virol.* 66:6288–6293 (1992).

Butera, et al., "Regulation of HIV–1 Expression by Cytokine Networks in a CD4$^+$ Model of Chronic Infection," *J. Immunol.* 150:625–634 (1993).

Ferre, et al., "Development and Validation of a Polymerase Chain Reaction Method for the Precise Quantitation of HIV–1 DAN in Blood Cells from Subjects Undergoing a 1–year Immunotherapeutic Treatment," *AIDS*, 7(Suppl. 2):S21–S27 (1993).

Holzer, et al., "Frequency of Cells Positive for HIV–1 p24 Antigen Assessed By Flow Cytometry," *AIDS*, 7(supp. 2):S3–S5 (1993).

Kojima, et al., "Monitoring the Activity of Antiviral Therapy for HIV Infection Using a Polymerase Chain Reaction Method Coupled with Reverse Transcription," *AIDS*, 7(Suppl. 2):S101–S105 (1993).

Miles, et al., "Rapid Serologic Testing with Immune–Complex–Dissociated HIV p24 Antigen for Early Detection of HIV Infection in Neonates," *N. Engl. J. Med.*, 328:297–302 (1993).

Piatak, et al., "High Levels of HIV–1 in Plasma During All Stages of Infection Determined by Competitive PCS," *Science*, 259:1749–1754 (1993).

Tetali, et al., "Human Immunodeficiency Virus Type I RNA Detection in Peripheral Blood Mononuclear Cell by Polymerase Chain Reaction: Enhanced Sensitivity after Mitogenic Stimulation," *AIDS Res. Hu. Retrovir.*, 9:77–82 (1993).

Poli, et al., "Interleukin 1 Induces Expression of the Human Immunodeficiency Virus Alone and in Synergy with Interleukin 6 in Chronicaally Infected U1 Cells: Inhibition of Inductive Effects by Interleukin 1 Receptor Antagonist," *Proc. Natl. Acad. Sci. USA*, 91:108–112 (1994).

Ou, et al., "Rapid and Quantitative Detection of Enzymatically Amplified HIV–1 DNA Using Chemiluminescent Oligonucleotide Probes," *AIDS Res. Hu. Retrovir.*, 6:1323–1329 (1990).

Wei et al., 1995, Nature 373:117–122.

Ho et al., 1995, Nature 373:123–126.

Seshamma et al., 1992, J. Virol. Methods 40:331–346.

Clark et al., 1991, New Engl. J. Med. 324:954–960.

Daar et al., 1991, New Engl. J. Med. 324:961–964.

Aldovini and Walker, 1990, Tech, HIV Res. 2:15–29.

Legrand–Poels et al., 1990, AIDS Res. Hum. Retro. 6:1389–1397.

Gibco–BRL 1993–94 Life Technologies Catalogue, chapter 1, cell culture reagents and media.

Coombs et al., 1989, New Engl. J. Med. 321:1626–1631.

RAPID, DIRECT, AND QUALITATIVE METHOD FOR THE DETERMINATION OF THE NUMBER OF HIV-1-INFECTED PATIENT CELLS EMPLOYING REACTIVE OXYGEN INTERMEDIATE GENERATORS

This invention was made with Government support under Grant Nos. R37-22624, AI33322, TW-00018 and summer fellowship 5P-35-AG00086, awarded by the National Institutes of Health. The Government has certain rights in the invention.

FIELD OF THE INVENTION

The present invention relates to a quantitative HIV virus analysis, and more particularly to a method for quantifying HIV virus in patient cells.

BACKGROUND OF THE INVENTION

The ability to monitor the progression of the HIV virus in patients is important in the study of HIV transmission, in predicting the onset and advancement of the AIDS disease, and evaluating the efficacy of treatments. Present methods available to the clinical laboratory for studying HIV pathogenesis and transmission rely on surrogate markers. Surrogate markers are biological indicators that tend to reflect, to varying extents, the gradual progression from symptomless HIV infection to full blown AIDS. Presently, the most commonly used markers are immune system cells known as CD4 cells, which are infected and destroyed by the HIV virus, and HIV p24 antigen. Other biological materials such as beta-2 microglobulin, neopterin, interferon, other cytokines and their receptors, and even early clinical symptoms are some of the alternative markers which are being investigated.

The use of markers to evaluate HIV progression has a number of limitations. No known marker consistently reflects disease progression in all individuals. For example, quantitation of serum HIV p24 antigen is insensitive, because up to 60% of patients may not have detectable levels of p24 even using the immune complex dissociation assay. Measurement of absolute CD4+ T cells in persons given anti-retroviral therapy is increasingly being viewed as an inaccurate indicator of disease progression. Furthermore, co-infection with human T-cell leukemia virus (HTLV), which is prevalent in certain areas, is likely to further impair the reliability of CD4+ T cells as a marker for the HIV virus.

In addition, by overemphasizing one preferred marker such as CD4, researchers risk overlooking an effective treatment if the treatment happens not to affect the marker chosen. Although a marker must have a biologically plausible connection to disease progression, the connection cannot effectively be utilized in treatment evaluation unless the marker also responds quickly to effective treatment. The use of combinations of markers may cure some of these deficiencies, but not without a corresponding increase in complexity and potential for error.

Determining the total amount of HIV virus present in a person's system at a given time, i.e., the "viral load," has been suggested as a better way of predicting the progress of infection. The present methods for assessing viral load, however, are unsatisfactory. HIV gene amplification by polymerase chain reaction (PCR) is sensitive, but PCR-amplified products are highly susceptible to cross-contamination, making this method impractical for general clinical use. Plasma viral culture methods are complicated and susceptible to contamination. Such methods quantitate overall viral production in the patient, but do not enumerate the number of cells infected.

An alternative to PCR amplification and plasma viral culture is the cell dilutional viral co-culture method. In the co-culture method, HIV-seronegative donor cells (peripheral blood mononuclear cells (PBMCs)) are first stimulated with phytohemagglutinin (PHA), and then co-cultured with dilutions of patient PBMCs, generally for at least 21 days. In addition to requiring donor PBMCs, the co-culture method is labor intensive, and requires a frequent exchange of culture medium (every 3 to 4 days), increasing the possibility of microbial contamination.

Various stimuli are known to induce expression of HIV, including antigens, mitogens, UV radiation, and phorbol esters. Phorbol myristate acetate has been shown to increase HIV production in chronically infected clone cell lines, as described, for example, in Folks, et al., *Characterization of a Promonocyte Clone Chronically Infected with HIV and Inducible By 13-Phorbol-12-Myristate Acetate*, J. Immunol., v. 140, pp. 1117–22 (1988); Kinter, et al., *Direct and Cytokine-Mediated Activation of Protein Kinase C Induces Human Immunodeficiency Virus Expression in Chronically Infected Promonocytic Cells*, J. Virol., v. 64, pp. 4306–12 (1990); and Poli, et al., *Interferon-α But Not AZT Suppresses HIV Expression in Chronically Infected Cell Lines*, Science, v. 244, pp. 575–77 (1988). Also, stimulation of patients' PBMCs with PHA in combination with phorbol 12-myristate 13-acetate has resulted in augmentation of p24 antigen level expression, as described in Tetali, et al., *Human Immunodeficiency Virus Type I RNA Detection in Peripheral Blood Mononuclear Cell by Polymerase Chain Reaction: Enhanced Sensitivity after Mitogenic Stimulation*, AIDS Res. Hu. Retrovir., v. 9, pp. 77–82 (1993). The combined use of PHA and PMA on human PBMCs was intended to induce sufficient viral production for detection by mRNA PCR. p24 antigen production was measured in a few of the samples, however, the results were not correlated with patients' stage of disease.

In view of the above-noted deficiencies and complexities of the prior methods for assessing viral load, the need remains for a straightforward, rapid technique for determining HIV viral load.

SUMMARY OF THE INVENTION

The present invention relates to a method for quantifying HIV p24 antigen in patient cells and determining HIV viral load. The method employs patient cells in a culture medium, which is substantially free of phytohemagglutinin (PHA). The cells are subjected to oxidative stress to stimulate HIV virus activation and production of HIV p24 antigen. The amount of HIV P24 antigen present in and associated with the patient cells is then measured.

In another embodiment of the invention, a culture medium containing the patient cells is prepared, and the cells are subjected to oxidative stress in the medium to activate HIV virus expression and HIV p24 antigen production. The amount of HIV p24 antigen present in and associated with the patient cells is measured, and the number of infected patient cells is quantified from the amount of HIV p24 antigen. The patient's viral load can then be determined by extrapolation.

In yet another embodiment of the invention, a culture medium containing the patient cells is prepared, and the cells are subjected to oxidative stress in the medium to activate HIV virus expression and HIV p24 antigen production. The culture medium is then separated into cell pellet and supernatant fractions, and the amounts of HIV p24 antigen present in and associated with said patient cells in said cell pellet and said supernatant fractions are measured.

The method of the invention has several advantages over prior techniques, including simplicity, speed, elimination of the need for donor cells, and the ability to quantitate viral load. For example, the prior co-culture method generally requires 21 or more days, and reliable detection of HIV p24 antigen from culture supernatants in the prior co-culture method requires a minimum of 10 to 14 days. In contrast, the method of the invention can be completed in 7 or fewer days.

The method of the invention is also less complicated and less subject to contamination than prior methods for assessing viral load. For example, unlike the viral co-culture method, the method of the invention requires no donor PBMCs, and no change of culture media. Cultivation of HIV from patient cells without co-cultivation with donor cells, as in the method of the invention, eliminates the potential for contamination of assay samples with HIV infected donor cells obtained from a donor who is testing seronegative. The potential for this type of contamination is significant in countries with a high prevalence of HIV infection. Furthermore, in populations where HIV vaccines are tested and serologic assays may not discriminate between vaccine or infection-induced antibodies, the method of the invention can determine true infection rapidly.

DETAILED DESCRIPTION OF THE INVENTION

Figure 1:
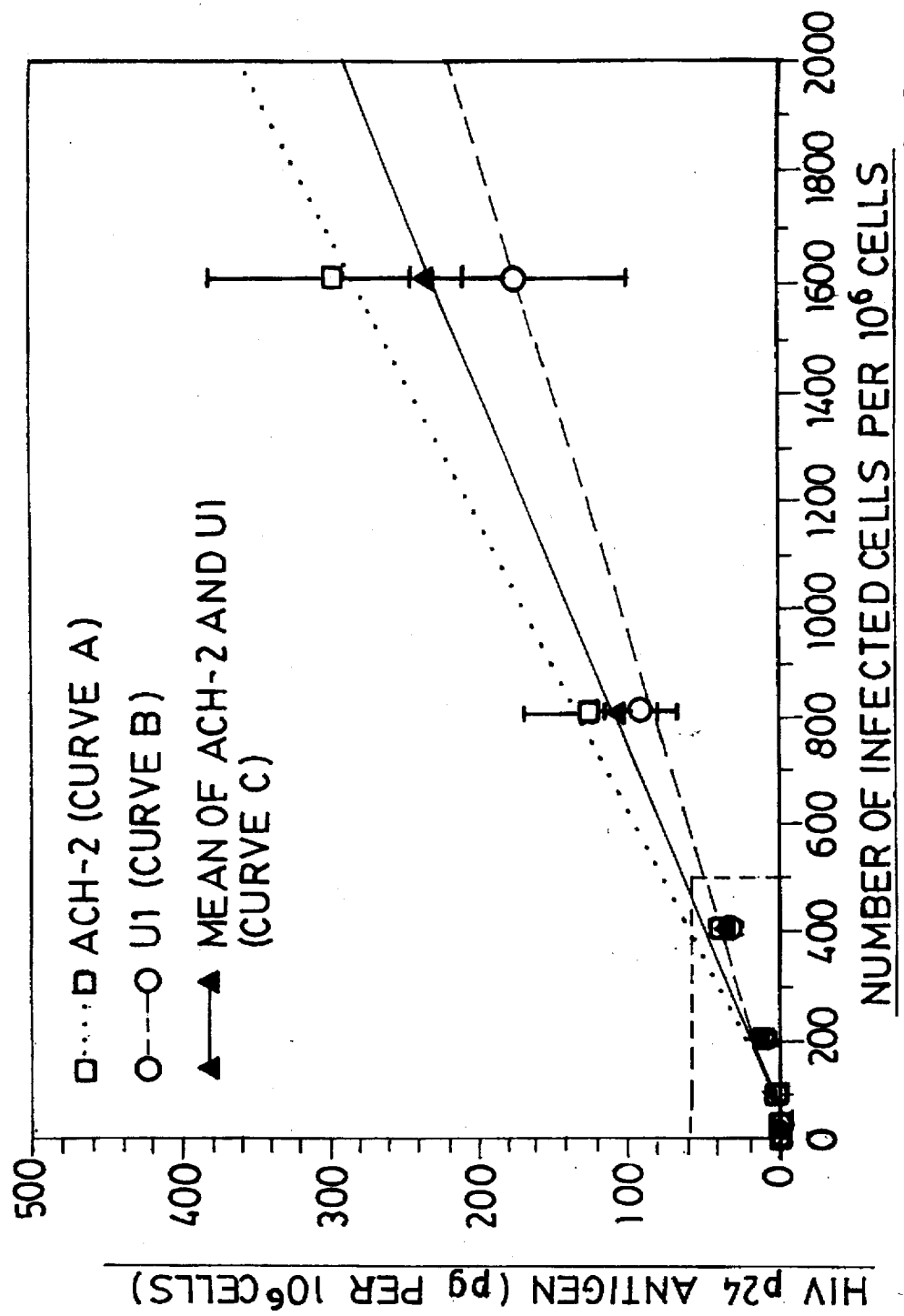
FIG. 1 is a plot of HIV p24 antigen (pg per $10^6$ cells) versus the number of infected cells for ACH-2 and U1 cell lines for cell dilutions up to 1600 HIV chronically infected cells per $10^6$ cells.

As described above, the present invention is directed to a method for quantifying HIV virus in patient cells. The method includes the steps of preparing a culture medium comprising the patient cells, oxidatively stressing the cells to stimulate HIV virus activation and HIV p24 antigen production, and measuring the amount of HIV p24 antigen present in and associated with the cells. The culture medium is preferably substantially free of phytohemagglutinin (PHA).

In other aspects of the invention, the number of infected patient cells is quantified from the amount of p24 antigen present in culture supernatants, cell pellets or both fractions. The number of infected patient cells can then be extrapolated to determine the patient's viral load.

The method of the invention may be used to quantify HIV virus in various types of patient cells, including peripheral blood mononuclear cells (PBMCs), bone marrow cells, lymph node cells, and cerebral spinal fluid cells. PBMCs are preferred, because they are the major population of cells susceptible to HIV infection during their circulation through all the body's organs, and provide a dynamic picture of HIV viral burden. Furthermore, circulating PBMCs are easily sampled by venipuncture. Patient cells may be present in the culture medium in a concentration of from about $0.5 \times 10^6$ to about $2 \times 10^6$ cells per ml, preferably about $10^6$ cells per ml.

Patient PBMCs may be obtained from heparinized peripheral blood collected by venipuncture. PBMC samples, preferably isolated within 24 hours by Ficoll-Hypaque (9%:33.9%) gradient centrifugation, and washed, for example, with Dulbecco's phosphate buffered saline (PBS) or normal saline (NS), are then resuspended in complete medium. The PBMCs may be present in the culture medium in a concentration of from about $0.5 \times 10^6$ to about $2 \times 10^6$ cells per ml, preferably about $1 \times 10^6$ cells per ml.

Other cells are obtained as follows by cell type and conventional method: bone marrow cells by aspiration of bone marrow, cerebral spinal fluid cells by intrathecal tap, and lymph node cells by biopsy. Bone marrow and spinal fluid cells are in suspension while lymph node cells need disection and dispersion through a fine mesh stainless steel tissue separator-mesh. Once in suspension, these cells are handled as PBMCs.

The primary component of the culture medium may consist of commercially available media, such as RPMI (Roswell Park Memorial Institute) medium, Click's medium, and Dulbecco Modified Eagle Medium. Various additives may be added individually or in combination to the culture medium. These additives include antibiotics used to minimize the potential for bacterial contamination of the medium, such as penicillin in a concentration range of approximately 20 to 250 units per ml, preferably approximately 100 units per ml, and/or streptomycin in a concentration range of approximately 20 to 250 micrograms per ml, preferably about 100 micrograms per ml. Ampicillin and gentamicin are alternative suitable antibiotics, and may be used in combination. The preferred concentration range for ampicillin is approximately 10 to 100 µg per ml, preferably 25 µg/ml; gentamicin is preferably used in a concentration range of approximately 2 to 20 µg/ml, preferably 5 µg/ml. Other suitable additives include polybrene in a concentration range of from about 0.2 µg/ml to about 5 µg/ml, preferably about 2 µg/ml, fresh L-glutamine in a concentration range of about 0.2 to 10 mM, preferably about 2 mM. Buffering agents, such as N-2 hydroxy-piperazine-$XI^1$-2-ethenesulfonic acid (hereafter "HEPES") buffer in a concentration of from 10 to 60 mM, preferably about 25 mM, and sodium bicarbonate ($NaHCO_3$) in a concentration range of about 0 to 25 mM may be added to the medium, as well as 2-mercaptoethanol in a concentration range of from about 0 to $5 \times 10^5$ molar. One or more nutrient sources, such as fetal bovine serum (FBS) which has been heat-inactivated by, for example, applying heat at 56° C. for 30 minutes may also be added to the medium. Suitable FBS concentrations in the culture medium are from about 2% to about 15% of the total culture volume, preferably 10%. Other suitable nutrient sources include synthetic serum, amino acids, composites of amino acids, growth factors, composites of growth factors, and mixtures thereof or with FBS.

The patient cells in the culture medium are then subjected to oxidative stress. "Oxidative stress" is exposure to a reactive oxygen intermediate generator, such as superoxide anion ($O_2^-$), hydrogen peroxide ($H_2O_2$), hydroxyl radical (OH·) and singlet oxygen ($^1O_2$). In the method of the invention, these reactive species induce expression of HIV virus in the patient cells, triggering a corresponding increase in the production of HIV p24 antigen.

Exposure of the patient cells to a reactive oxygen intermediate generator may be accomplished by adding an exogenous oxygen generator, such as glucose, glucose oxidase, hydrogen peroxide or compounds capable of releasing hydrogen peroxide, superoxide, or mixtures thereof to the culture medium. Glucose oxidase may be added to the medium in an amount of from about 5 to about 25 U/ml. Glucose, hydrogen peroxide, compounds capable of releasing hydrogen peroxide, superoxide, or mixtures thereof may be added to the medium in an amount of from about 1 nM to about 100 mM. Alternatively, the medium may include one or more phorbol esters, specifically those which induce intracellular oxygen radical generation and/or activation of protein kinase C, in an amount of from 10 to 50 ng/ml medium. Among the phorbol esters, phorbol-12-myristate-13-acetate (PMA) is particularly preferred.

Incubation of test samples following preparation of the patient cell culture medium, including the reactive oxygen intermediate generator, may be carried out for a period of from about 5 to about 8 days, preferably 7 days, at a temperature of from about 25° to about 37° C., preferably about 35° to about 37° C. A humidity of from about 90% to about 95%, and an atmospheric carbon dioxide concentration of about 5%, are preferred for incubation, but incubation may be carried out at humidities of from about 80% to about 98% and at atmospheric carbon dioxide concentrations of from about 3% to about 6%.

Various types of culture containers, including culture tubes, flasks, and wells may be used. However, the preferred culture containers are loosely capped conical centrifuge tubes, tilted at about a 45° angle for incubation, or specially manufactured vessels which mimic the same.

In addition to the reactive oxygen intermediate generator, one or more cytokines may be introduced into the culture medium. Suitable cytokines, which may be used individually or in combination, include interleukin-2 (IL-2), tumor necrosis factor-α, interleukin-1 (IL-1), and interleukin-6 (IL-6). The total cytokine concentration in the culture medium may range from 0 to about 50 ng/ml, preferably from about 1 ng/ml to about 5 ng/ml. For IL-2, 10 to 20 U/ml of activity is preferable. The addition of one or more cytokines appears to increase the sensitivity of the method. The use of interleukin-2 in conjunction with phorbol 12-myristate 13-acetate is particularly preferred.

Without being bound by theory, it appears that in the culture medium of the method of the invention, PMA provides the signal for HIV replication that replaces PHA-stimulated donor cells in the prior viral co-culture method. IL-2 in the culture medium probably serves to maintain cell growth, while PMA triggers viral replication as described in Folks, et al., *Characterization of a Promonocyte Clone Chronically Infected With HIV and Inducible By 13-Phorbol 12-Myristate Acetate*, J. Immunol, v. 140, pp. 1117–1122 (1988); Kinter, et al., *Direct and Cytokine-Mediated Activation of Protein Kinase C Induces Immunodeficiency Virus Expression In Chronically Infected Promonocytic Cells*, J. Virol., v. 64, pp. 4306–4312 (1990); and Poli, et al., *Interferon-α But Not AZT Suppresses HIV Expression In Chronically Infected Cell Lines*, Science, v. 244, pp. 575–577 (1989). This is based on the inability of IL-2 to stimulate p24 production by HIV-seropositive patient cells without co-culture with PHA-stimulated donor PBMCs as described in Poli, et al., *The Effect Of Cytokines and Pharmacologic Agents On Chronic HIV Infection*, AIDS Res. Hum. Retroviruses, v. 8, pp. 191–197 (1992). The signals transducing PMA include activation of protein kinase C as described in Ho, et al., *Protein Kinase C Activity Is Diminished In Tetanus Toxin-Treated Macrophages and In the Spinal Cord of Mice Manifesting Generalized Tetanus Intoxication*, J. Infect. Dis., v. 157, pp. 925–933 (1988) and Kinter, et al., supra; induction of oxygen radical production as described in Schreck, et al., *Reactive Oxygen Intermediates As Apparently Widely Used Messengers In the Activation of the NF-κB Transcription Factor and HIV-1*, EMBO. J., v. 10, pp. 2247–2258 (1991); production of tumor necrosis factor alpha and other cytokines as described in Poli, et al., AIDS Res. Hum. Retroviruses, v. 8, supra; and expression of IL-2 receptor, resulting in increased sensitivity to IL-2 as described in Valge, et al., *Protein Kinase C Is Required For Responses to T Cell Receptor Ligands But Not To Interleukin-2 in T Cells*, Cell, v. 55, pp. 101–112 (1988). These factors in turn activate the transcriptional enhancer nucleus-binding protein, NF-$_κ$B as described in Cullen, et al., *Regulatory Pathways Governing HIV-1 Replication*, Cell, v. 58, pp. 423–426 (1989); Duh, et al., *Tumor Necrosis Factor-α Activates Human Immuno-deficiency Virus Type-1 Through Induction of Nuclear Factor Binding to the NF-kB Sites in the Long Terminal Repeat*, Proc. Natl. Acad. Sci. U.S.A., v. 86, pp. 5974–5978 (1989); Legrand-Poels, et al., *Activation of Human Immunodeficiency Virus Type 1 by Oxidative Stress*, AIDS Res. Hum. Retroviruses, v. 6, pp. 1389–1397 (1990); Tucker, *Biology of Disease. Endothelial Nuclear Factor-kB and the Initiation of the Atherosclerotic Lesion*, Lab. Invest., v. 68, pp. 499–508 (1993); Poli, et al., AIDS Res. Hum. Retroviruses, v. 8, supra; and Schreck, et al., EMBO J., v. 10 supra. NF-$_κ$B binds to specific DNA sequences in the long terminal repeat region of HIV and increases HIV transcription as described in Cullen, et al., Cell, v. 58, supra; Duh, et al., supra; and Poli, et al., AIDS Res. Hum. Retroviruses, v. 8, supra.

Following incubation, cells may be separated from the culture medium by centrifugation, and the supernatant is preferably removed and saved. A small known amount, preferably 900 microliter or less, of fresh medium is then added back to suspend the cell pellet.

The cells are then lysed to release intracellular p24 antigen. This may be accomplished by adding a lysing agent such as Triton X-100™ or Noredit NP 40 to the samples at a preferred final concentration of 0.2% by volume and incubating the samples for a short period. Samples may then be rapidly and repeatedly frozen and thawed, for example, in dry ice/ethanol (−70° C.) and water (37° C.) baths, respectively, to further disrupt the cells and cell nuclei. Released intracellular p24 antigen may then be recovered after centrifugation of samples to remove cellular debris.

The rapid HIV culture method of the invention may be used to detect the presence of HIV virus in patient samples, for example, by using a commercial solid-phase enzyme immunoassay (EIA), available from Coulter Corporation, Hialeah, Fla. The presence of captured p24 antigen is detected by an enzyme immunoassay technique. A p24 antigen neutralization kit, also available from Coulter Corporation, can also be used to detect or confirm HIV positive samples. A neutralization kit can be used to determine the extent to which neutralization reagent antibodies prevent binding of sample p24 antigen to monoclonal antibodies. The kit is used to block the capture of p24 antigen present in the patient sample. Comparison with untreated sample demonstrates that the detection of p24 antigen is specific. HIV p24 antigen supplied, for example, with an HIV p24 antigen kit, may be used to prepare a standard curve from which the p24 antigen concentration of experimental samples can be determined from the optical density readings of the EIA.

Released (supernatant) and intracellular (cell pellet) p24 antigen may be assayed separately by commercial EIA. However, the sensitivity of the method is improved when the sum of the p24 antigen values for the released and intracellular fractions is employed, as described in the Examples below.

By comparing the quantity of virus produced in infected cells in the method of the invention to the amount of virus produced in HIV chronically infected cell lines, for example, in U1 monocytes and ACH-2 lymphocytes stimulated under corresponding conditions, the approximate number of infected patient cells can be calculated.

Alternatively, flow cytometry can be used to detect and quantitate intracellular HIV virus.

The method of the invention is illustrated by the following Examples.

EXAMPLES

Materials

RPMI (Roswell Park Memorial Institute) culture medium (RPMI 1640), penicillin/streptomycin, L-Glutamine, Dulbecco's phosphate buffered saline (PBS), and fetal bovine serum (FBS) were obtained from GIBCO Laboratories, Grand island, N.Y. N-2 hydroxy-piperazine-XI$^1$-2-ethenesulfonic acid (HEPES) buffer solution was purchased from Whittaker Bioproducts, Inc., Walkersville, Md. Conical centrifuge tubes (50 cc) and interleukin-2 were purchased from Becton Dickinson, Bedford, Mass., and phytohemagglutinin (PHA), ficoll, polybrene, and phorbol-12-myristate-13-acetate (PMA) were obtained from Sigma Chemical Co., St. Louis Mo. Tissue culture flasks (25 cm$^2$) and 24-well tissue culture plates were obtained from Corning Glass Works, Corning, N.Y., and 76% Hypaque was obtained from Winthrop Pharmaceutical, New York, N.Y. Sterile water and NaCl solution (NS) (0.9%) were obtained from Abbott Laboratories, North Chicago, Ill., and anti-p24 antigen phycoerythrin-labelled monoclonal antibodies (KC57-RD1) and an HIV-1 p24 antigen detection kit and neutralization assay were obtained from Coulter Corporation, Hialeah, Fla. 20% Triton X-100 lysing agent was obtained from Sigma Chemical Co., St. Louis, Mo.

HIV chronically infected cell lines, namely a monocyte cell line (U1) and a T cell clone (ACH-2), were obtained from Dr. Thomas Folks, Centers for Disease Control and Prevention, Atlanta, Ga. U937 and A3.01 parent cell lines not infected with HIV, from which U1 and ACH-2 were respectively derived. See Folks, et al., *Characterization of a Continuous T-Cell Line Susceptible to the Cytopathic Effects of the Acquired Immunodeficiency Syndrome (AIDS)-Associated Retrovirus*, Proc. Natl. Acad. Sci. U.S.A., v. 82, pp. 4539–43 (1985), Folks, et al., *Cytokine Induced Expression of HIV-1 in a Chronically Infected Promonocyte Line*, Science, v. 238, pp. 800–802 (1987), and Folks, et al., *Characterization of a Promonocyte Clone Chronically Infected With HIV and Inducible By 13-Phorbol-12-Myristate Acetate*, J. Immunol., v. 140, pp. 1117–22 (1988) were obtained from American Type Culture Collection, Rockville, Md., and Dr. Folks, respectively.

Example 1

Preparation of Materials

Isolation of HIV seropositive and seronegative donor cells

Heparinized (50 U/ml) peripheral blood (15 ml) was collected by venipuncture from 24 patients, 23 of whom were HIV seropositive, from the New York Hospital wards and Center for Special Studies. Of the 23-HIV seropositive patients, 22 were adults (54% men), and one was a male child (patient 23) infected by vertical transmission; 18 were symptom-free and 5 had AIDS-defining illness (patients 1, 2, 3, 23, and 24). One HIV-seronegative patient (patient 9) studied presented with Guillain-Barré syndrome following high risk homosexual activity and had mild pleocytosis on cerebral spinal fluid examination.

To determine the specificity of the method of the invention, blood from HIV-seronegative healthy volunteers or donors from the New York Blood Center was collected as heparinized peripheral blood or citrate leukocyte rich buffy coats, respectively.

Each sample of peripheral blood mononuclear cells (PBMCs) was isolated within 24 hours by 9% Ficoll-33.9% Hypaque gradient centrifugation as described in Ho, et al., *Protein Kinase C Activity is Diminished in Tetanus Toxin-Treated Macrophages and in the Spinal Cord of Mice Manifesting Generalized Tetanus Intoxication*, J. Infect. Dis., v. 157, pp. 925–933 (1988), washed twice with PBS, and resuspended in complete medium containing RPMI 1640, 10% FBS, 2 mM L-glutamine, 100 U/ml penicillin, 100 µg/ml streptomycin, and 25 mM HEPES.

Example 2

Rapid HIV Culture Method (Invention) and Isolation of 224 Antigen

HIV-seropositive patient PBMCs were suspended in complete media (10 ml) containing 10% IL-2 (20 U/ml), PMA (50 ng/ml), and polybrene (2 µg/ml) in 50 cc centrifuge tubes. Loosely capped tubes were incubated at a 45 degree angle at 37° C., at an atmospheric $CO_2$ concentration of 5% and an atmospheric humidity of approximately 90% for a period of 7 days. Cells were then spun at 175×gravity (1000 RPM) for 5 minutes, and the sample supernatants containing extracellular p24 antigen were removed and saved. For each sample, 900 µl of fresh medium was added to the cell pellet, and the suspended cells were transferred to 1.5 ml Eppendorf tubes.

20% Triton X-100 (10 µl ) was added to each of the sample tubes and the samples were incubated at room temperature for 15 minutes to lyse the cells and release intracellular p24 antigen. The samples were frozen at −70° C. in a dry ice/EtOH bath and thawed in a 37° C. water bath 3 times at 3 minutes per cycle. The samples were then spun in a microcentrifuge at 7,000×gravity (10,000 RPM) for 5 minutes and the supernatants containing intracellular p24 antigen were transferred to fresh Eppendorf tubes. The samples containing released and intracellular p24 antigen were stored at −70° C. for subsequent p24 assays.

Example 3

Standard Quantitative viral Co-Culture of Patient PBMCs (Comparison)

HIV-seronegative donor PBMCs were suspended in complete medium at $3\times10^6$ to $5\times10^6$ cells per ml and stimulated with PHA (2 µg/ml) for 24 hours at 37° C. in a 5% $CO_2$ atmosphere. To quantitate the cell-associated HIV virus, PHA-stimulated donor PBMCs ($2\times10^6$) were co-cultured with 10-fold dilutions of patient PBMCs ($2\times10^6$ to $2\times10^1$) in RPMI 1640 medium (1.5 ml) containing 10% IL-2, at 37° C. in a 5% $CO_2$ atmosphere, in 24 well tissue culture plates, as described in Ho, et al., *Quantitation of Human Immunodeficiency Virus Type I in the Blood of Infected Persons*, v. 321, pp. 1621–25 (1989). After 24 hours and subsequently every 3 days (for 21 days), half of the supernatant in each sample was removed, saved, and replaced with a half volume fresh medium containing 10% IL-2. The presence of HIV antigen in culture supernatants collected during the assay was determined by a commercial HIV antigen capture EIA, as described below. A positive co-culture for each dilution of patient cells was defined as p24 antigen values of either a) $\geq 30$ pg/ml and a later harvest value of at least four times greater than the first value or b) two consecutive harvest p24 antigen values of >250 pg/ml. In addition, when one or more supernatants were tested by a second EIA, all positive cultures were neutralized by a $\geq 50\%$.

Example 4

Detection of HIV p24 Antigen in Rapid HIV Culture (Invention) and Viral Co-Culture (Comparison) By Enzyme Immunoassay (EIA) Neutralization Assay HIV p24 viral antigen in the rapid HIV culture method of the invention and in the viral co-cultures used for comparison was measured by a commercial solid-phase enzyme immunoassay obtained from Coulter Corporation. Released (supernatant) and intracellular (cell pellet) p24 antigens were assayed separately. A 200 µl sample was considered reactive for p24 antigen when the absorbance detected at 450 nm by an EL 340 automated microplate reader (obtained from Bio-Tek Instruments, Inc., Winooski, Vt.) was greater than the cutoff value, i.e., 0.55+the absorbance of the mean negative control. Samples positive by EIA were then confirmed positive using a p24 antigen neutralization kit if antibodies in a neutralization reagent prevented binding of sample p24 antigen to monoclonal antibodies in the sample well by $\geq 50\%$ in a subsequent EIA.

A standard curve was prepared with the use of the HIV p24 antigen supplied with the HIV p24 antigen kit. Standards ranging from 7.8 to 250 pg p24 per ml were used in the EIA to estimate the concentration of p24 in experimental samples. The amount of p24 in the supernatant and cell pellet expressed as pg/ml was obtained from the standard curve for each assay. HIV p24 antigen in the supernatant and cell pellet, expressed as picograms per milliliter, is obtained from the standard curve for each assay. The rapid culture results are expressed as $pg/10^6$ cell to allow quantitation of number of HIV-infected patient cells when compared with chronically infected cell lines.

To derive the amount of p24 antigen produced by $10^6$ PBMCs, the following formula was used:

$$p24\ antigen/10^6\ PBMC = \frac{(p24\ antigen\ cell\ pellet) + (p24\ antigen\ supernatant) \times 10}{10}$$

where p24 antigen cell pellet is the total p24 in $10^7$ PBMC; p24 antigen supernatant is the amount of p24 antigen detected in one milliliter of supernatant, and since $10^7$ cells were cultured in 10 ml of medium, this value was multiplied by 10. The numerator is divided by 10 to adjust for p24 antigen per $10^6$ PBMC.

Example 5

Assessment of intracellular p24 antigen level

Isolated PBMCs or HIV-chronically infected cells were fixed in 20 µg/ml lysolecithin/1% paraformaldehyde for two minutes, cold 100% methanol for 15 minutes on ice, and 0.1% Noridet P-40 for five minutes on ice. No washes were performed between fixation steps. Fixed cells were stained with anti-p24 antigen phycoerythrin-labelled monoclonal (KC57-RD1, from Coulter Corporation) antibodies for 15 minutes and washed twice with PBS. The samples were analyzed by flow cytometry for the amount of red fluorescence per cell on an EPICS Profile II flow cytometer, from Coulter Corporation. For undiluted U1 cells, flow cytometry detected more than 50% of the cells expressing intracellular p24 antigen. For U1 cells diluted to 10% and 1%, flow cytometry detected intracellular p24 antigen in 10% and 1.6% of the cells, respectively. At the lower limit of detection, this value represented $10^4$ infected cells or 10,000 TCID per $10^6$. Because of the lower sensitivity, the flow cytometry was abandoned as a potential comparison for the HIV rapid-culture assay. Therefore, all the data and analysis described below is based on EIA results except where otherwise indicated.

Example 6

Quantitation of HIV Cell Infection Using HIV Chronically Infected Cell Lines Invention The number of cells infected with HIV was determined by comparing the amounts of p24 antigen detected in experimental samples with the p24 amounts produced in chronically infected U1 monocytes and ACH-2 T cells. Infected U1 and ACH-2 cells were maintained in continuous culture in complete medium (RPMI 1640, 2 mM L-glutamine, 100 U/ml penicillin, 25 mM HEPES, and 10% FBS-heat inactivated) for no more than 3 months. U1 cells (about $5\times10^6$) were harvested, washed twice in PBS and counted on a haemocytometer. The cells ($3.6\times10^6$) were resuspended in complete medium ($3.6\times10^6$ in 10 ml complete medium or $1.6\times10^6/5$ ml).

A three 10-fold dilution was prepared by adding 1 ml of the $1.6\times10^6/5$ ml cell suspension to fresh complete medium (9 ml) ($1.6\times10^5/5$ ml), followed by 1 ml of $1.6\times10^5/5$ ml into 9 ml of fresh medium ($1.6\times10^4/5$ ml) and dilution of 1 ml of $1.6\times10^4/5$ ml into 9 ml of fresh medium to arrive at $1.6\times10^5/5$ ml. Serial 2-fold dilutions were then prepared as follows: 5 ml of the $1.6\times10^3/5$ ml cell suspension was added to complete medium (5 ml) (T1600=1600 cells/200 µl). Six 50 ml centrifuge tubes (labeled "T800," "T400," "T200," "T100," "T50," and "T25") were filled with 5 ml complete medium. No cells are added to Tzero. T1600 suspension (5 ml) was added to the "T800" tube, and resuspended, and then 5 ml of the T800 suspension was added to the T400 tube. This process was repeated until 5 ml of the T50 suspension had been added to the T25 tube.

HIV negative U937 cells ($10^6$ cells) were resuspended in complete medium (4 ml) to obtain a concentration of $2.5\times 10^5$ cells/ml. This HIV-negative U937 suspension (4 ml) was added to each labeled tube, along with IL-2 (1 ml) for a final IL-2 concentration of 10%, and PMA (162 µl of 5 mM stock solution) for a final PMA concentration of 50 ng/ml. The U937 cells in each tube were thoroughly resuspended in this medium, and incubated on an incline for 2 days at 37° C. and 5% $CO_2$. After incubation, the cells were harvested according to the method described above in Example 2, except that cell lysis and release of intracellular p24 was carried out in complete medium (900 µl ). Cell pellets (obtained by centrifugation at 175×g for 5 minutes) and supernatants were then separately tested for p24 in an enzyme immunoassay as described above in Example 4. In this way, the proportion of p24 antigen in each component was determined. The same process was used with A3.01 cells. Regression analysis of the data was performed using EPI-INFO version 5.1 statistical analysis software.

Figure 2:
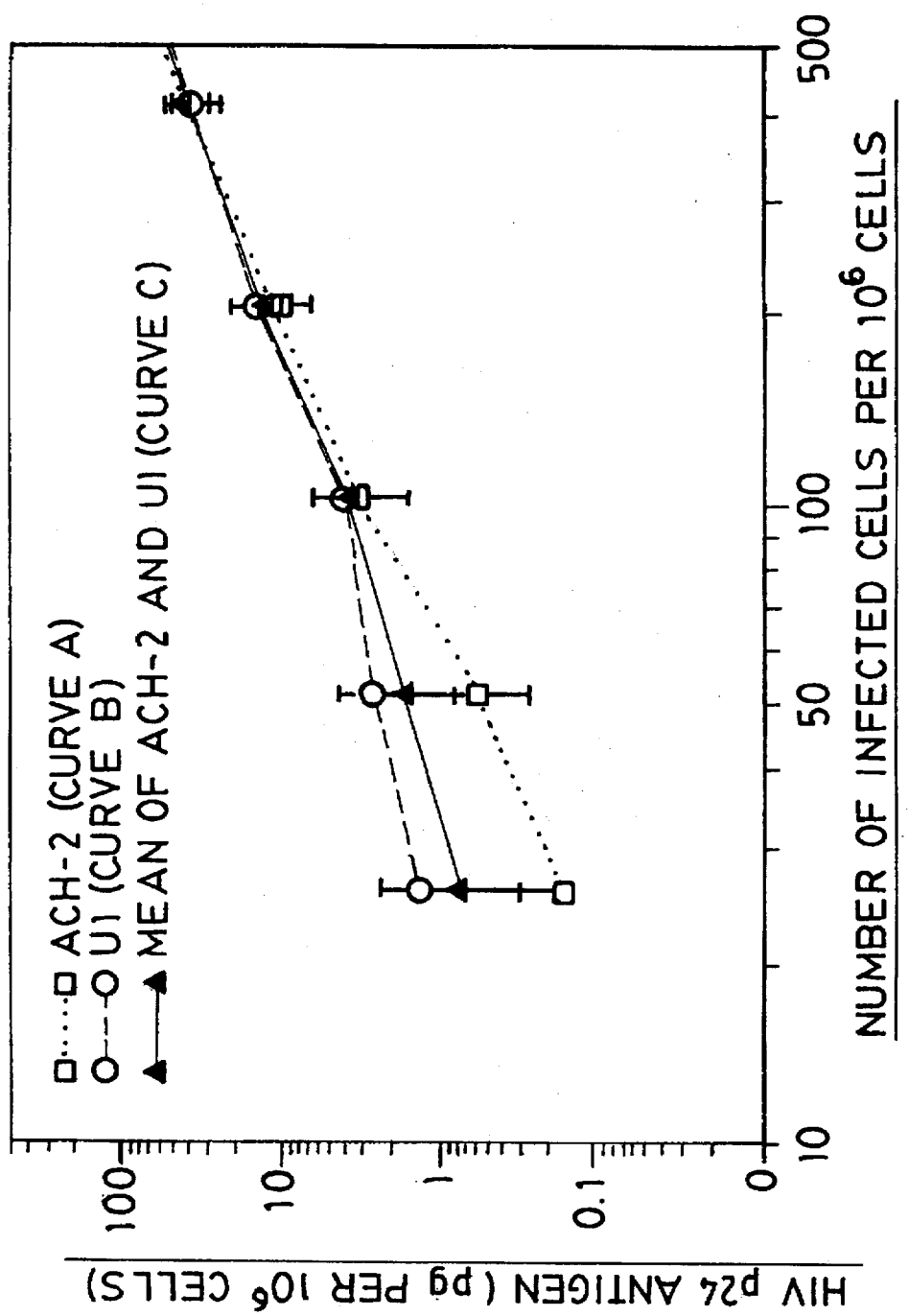
FIG. 2 is a plot of HIV p24 antigen (pg per $10^6$ cells) versus the number of infected cells for ACH-2 and U1 cell lines for cell dilutions up to 400 HIV chronically infected cells per $10^6$ cells.

U1 monocytic and ACH-2 T cells were used to reflect levels of HIV infection in monocytes and T cells. The amounts of p24 antigen produced by known numbers of these chronically HIV infected cells were used to generate a standard curve, whereby the number of HIV-infected patient PBMCs was determined. The numbers of cells infected with HIV in $10^7$ PBMCs was quantified by comparing the amounts of p24 antigen detected in patient cell cultures to that produced by known numbers of chronically infected T cells and monocytes used to construct standard curves. FIGS. 1 and 2 illustrate the production of p24 antigen by U1 monocytic and ACH-2 T cells cultured with $10^6$ parent cells not infected with HIV for cell dilutions up to 1600 and 400 HIV chronically infected cells per $10^6$ cells, respectively. The U1 cell standard curve (curve B in FIGS. 1 and 2) was prepared from the mean of U1 cultured with $10^6$ U937 parent cells not infected with HIV (n=6). The ACH-2 cell standard curve (curve A in FIGS. 1 and 2) was prepared from the mean of ACH-2 cells cultured with $10^6$ A3.01 parent cells not infected with HIV (n=6).

Although U1 and ACH-2 cell lines were used to represent T-cell and monocyte levels of HIV infection, the U937 cell line from which U1 was derived acts more like T cells than monocytes with regard to HIV infection and load. For this reason, it is not surprising that the level of HIV detected was similar when either cell line was used to generate a standard curve. However, in the absence of a true "standard," one or more of these cell lines can be used for construction of a standard curve to determine the number of HIV-infected patient PBMCs.

A standard curve of the mean of the p24 antigen produced by both U1 and ACH-2 cells was also constructed (curve C in FIGS. 1 and 2), as peripheral blood contains similar numbers of CD4+ T cells and monocytes, and both types of cells harbor HIV. U1 monocytes and ACH-2 T cells were equally weighted in constructing curve C, because the numbers of monocytes approximate those of CD4+ T cells in persons with absolute CD4+ T cells of 500 µl$^{-1}$.

Although not shown in FIG. 1, HIV p24 antigen was not detected in U1 or ACH-2 cells cultured for up to 72 hours in medium alone at cell concentrations below $10^4$ per well in a 24-well plate. However, in cultures prepared with PMA and IL-2, a linear relationship between numbers of infected U1 or ACH-2 cells and p24 antigen production was observed. Compared to U1 cells, ACH-2 cells produced slightly higher amounts of p24 antigen at higher HIV infected cell numbers, but U1 and ACH-2 cells produced comparable amounts of p24 antigen at cell counts of 400 or less cells per $10^6$ cells.

Of the 23 HIV seropositive persons, 22 had p24 antigen detected by the rapid culture method of the invention in either or both the supernatant and cell associated fractions, as shown in Table 1 below. Table 1 presents the relationships between patients' clinical stage of HIV infection, the detection of p24 antigen and numbers of HIV-infected cells detected by rapid and standard co-culture assays. Twenty of 23 (87%) were confirmed by neutralization and considered positive. Patient 10 was negative in the rapid culture because the p24 antigen EIA was non-reactive. For patients 15 and 19, the first p24 antigen EIA assay of the rapid culture was reactive but neutralized by <50% in the second EIA, and the culture was considered negative (Table 1).

TABLE 1

Comparison between rapid HIV culture (RHC) and 21-day co-culture assays.

| Cell Patient[a] | HIV p24 Ag[b] (pg/$10^6$ cells)[c] RHC | Viral quantitation (TCID per $10^6$ PBMC)[d]: | | | | Absolute CD4 + T count per |
|---|---|---|---|---|---|---|
| | | Rapid HIV culture: | | | 21 Day HIV | |
| | | A | B | C | co-culture | |
| 1 | 26.4 | 320 | 320 | 400 | 50 | 10 |
| 2 | 1.8 | 40 | 70 | 40 | 50 | 90 |
| 3 | 5.4 | 120 | 120 | 120 | 5 | 696 |
| 4 | 1.4 | 25 | 60 | 40 | ND | 150 |
| 5 | 6.9 | 130 | 150 | 120 | 50 | 765 |
| 6 | 24.5 | 300 | 300 | 400 | 500 | 190 |
| 7 | 2.9 | 90 | 90 | 80 | 50 | 636 |
| 8 | 18.9 | 240 | 250 | 300 | 500 | 440 |
| 9 | 12.0 | 170 | 200 | 200 | NEG | NA |
| 10 | 0.0 | 0 | 0 | 0 | 5 | 319 |
| 11 | 20.7 | 260 | 260 | 260 | 50 | 284 |
| 12 | 7.2 | 150 | 150 | 145 | 50 | 266 |
| 13 | 505.0 | 4100 | 2700 | 3400 | 500 | 420 |
| 14 | 85.4 | 750 | 500 | 650 | ND | 157 |
| 15 | 7.8 | 140 | 160 | 150 | 500 | 366 |
| 16 | 66.2 | 680 | 450 | 300 | ND | 300 |
| 17 | 8.3 | 145 | 165 | 155 | 5 | 150 |
| 18 | 23.5 | 280 | 280 | 280 | 5 | 90 |
| 19 | 5.8 | 125 | 125 | 125 | 5 | 290 |
| 20 | 5.4 | 120 | 120 | 120 | 5 | 30 |
| 21 | 7.1 | 145 | 145 | 145 | 5 | 624 |
| 22 | 22.2 | 275 | 275 | 275 | 5 | 435 |
| 23 | 13.1 | 190 | 210 | 195 | 5 | 37 |
| 24 | 8.9 | 150 | 170 | 160 | ND | NA |

[a]Patients 1, 2, 3, 23 and 24 had AIDS-defining illness; patient 23 was the only child tested. Patient 9 had Guillain-Barré syndrome and was HIV seronegative. Patients 10, 15, and 19 were rapid HIV culture negative. Patient 10 was non-reactive to p24 antigen EIA; patients 15 and 19 had positive EIA for p24 antigen but did not neutralize by ≧ 50% on a second EIA.
[b]Abbreviations: Ag, antigen; RHC, rapid HIV culture; ND, not done because of insufficient cells; NEG, negative; NA, not available.
[c]HIV p24 antigen in the rapid culture method of the invention was measured by EIA, and is expressed as picograms per $10^6$ cells. For each patient, the amount reported is the sum of released and intracellular fractions. Of the 20 positive rapid HIV cultures, 3 (15%) were positive only in the cell-associated fraction and the remainder were positive in both cell-associated and supernatant fractions.
[d]for the rapid culture method of the invention, the tissue culture infective dose (TCID) was determined using the standard curves prepared as described above using HIV chronically infected monocytic U1 and ACH-2 T cell lines, and the mean of the two cell lines (columns A, B, and C, respectively). The U1 cell standard curve (A) was prepared from the mean of U1 cultured with $10^6$ U937 parent cells not infected with HIV (n = 6). The ACH-2 cell standard curve (B) was prepared from the mean of ACH-2 cells cultured with $10^6$ A3.01 parent cells not infected with HIV (n = 6). Standard curve C is the mean of U1 and ACH-2 cells (C). For the 21 day co-culture 10-fold dilutions of patients' PBMCs where co-cultured with 2 × $10^6$ PHA-stimulated HIV seronegative donor cells, and the lowest dilution of patient's cells in which HIV antigen was detected in the culture supernatants was expressed as TCID.
[e]For each patient, the available absolute T cell count determined by flow cytometry is provided. Flow cytometry was performed by The New York Hospital Clinical Laboratory, which participates in the national and CDC sponsored proficiency testing and is certified to perform T cell subset quantitations.

As described above and shown in Table 1, the rapid HIV culture method of the invention was used to evaluate the HIV viral load in 23 HIV seropositive individuals, 11 HIV seronegative individuals with low risk for HIV, and on one HIV seronegative patient who was participating in high risk homosexual activities and was found to have developed Guillain-Barré syndrome with low level pleocytosis on examination of the cerebral spinal fluid. Of the 23 HIV-seropositive patients, 22 were adults (54% were men) and one was a boy infected by vertical transmission. Seven had CD4+ T cells below 200 µl and five had clinical AIDS. The remaining patients were symptom-free with HIV infection.

HIV p24 antigen of the rapid culture is expressed as pg per $10^6$ cells and is the sum of released and intracellular fractions. Of the positive rapid HIV cultures, 3 of 22 (15%) were positive only in the cell associated fraction and the remainder were positive in both cell associated and supernatant fractions.

As Table 1 shows, 22 of the 23 HIV seropositive patients had p24 antigen detected by the method of the invention in either or both the supernatant and cell-associated fractions. On the second EIA assay for p24 antigen, samples from 20 of the 23 seropositive patients, or 87%, were neutralized as described above by free monoclonal antibody and considered positive. HIV p24 antigen was detected in the initial EIA in two of the remaining samples from seropositive individuals, but were considered negative because both were neutralized by less than 50% in the second EIA.

Each of the 11 HIV seronegative low risk persons who served as controls were determined in the method of the invention to be negative after testing by the second EIA. Three of the 11 samples from seronegative individuals had optical density optical density units that were slightly above background in the first EIA (negative control of the kit) and all 11 were negative in the second EIA. The rapid culture method of the invention gave a positive result for the HIV seronegative patient with Guillain-Barré syndrome, i.e., the p24 antigen was neutralized with the competing p24 monoclonal antibody in a second EIA, as described above in Example 4.

Of the 23 samples obtained from seropositive patients for testing in the rapid culture method of the invention, 19 samples contained sufficient cells left for comparison of the method of the invention with the 21 day co-culture assay. Each of the seropositive patients tested by the 21 day co-culture method were found positive. For the HIV seronegative patient with Guillain-Barré syndrome, the rapid HIV culture was positive, while the 21 day co-culture was negative.

Figure 3:
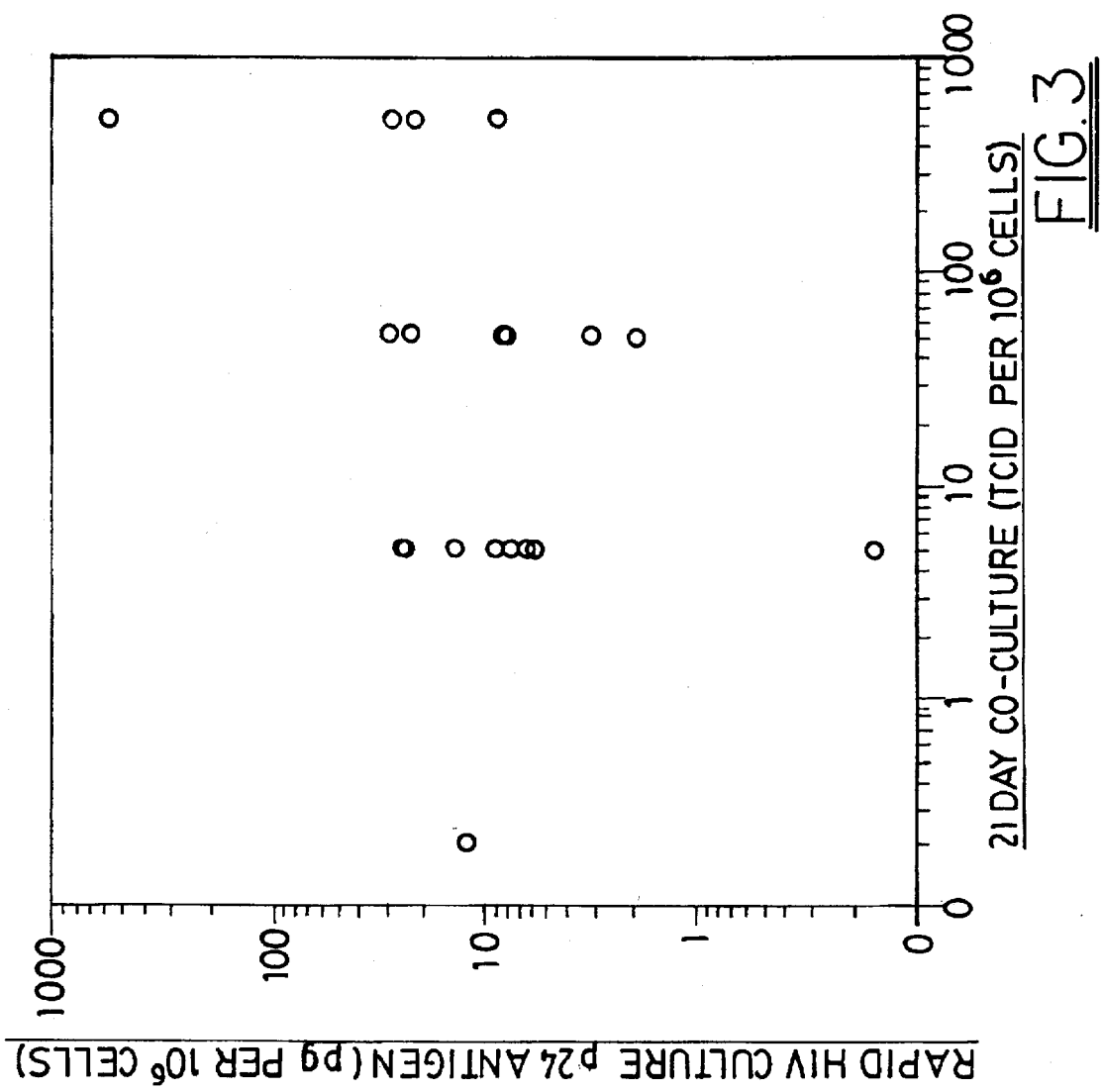
FIG. 3 is a plot of HIV p24 antigen (pg per $10^6$ cells) detected in the method of the invention versus the tissue culture infective dose (TCID) per $10^6$ PBMC determined by the prior 21 day co-culture method.

FIG. 3 compares the amount of HIV p24 antigen detected by the rapid HIV culture assay of the invention in $10^6$ PBMC from HIV seropositive patients, as described above in Examples 2, 4 and 5, to the tissue culture infective dose (TCID) per $10^6$ PBMC determined by the prior 21 day co-culture method, as described above in Example 3. As described above, the lowest dilution of a patient's cell in which HIV antigen was detected in the 21 day co-culture supernatants was expressed as TCID. As FIG. 3 shows, a positive relationship was observed between the method of the invention and the 21 day co-culture method, as increasing amounts of p24 antigen per $10^6$ PBMC paralleled higher TCID per $10^6$ PBMC. The Pearson correlation coefficient was 0.55 (95% confidence interval, 0.16 to 0.80, P<0.02).

By using the standard curve C that was generated with data from both T cells and monocytes, comparable numbers of HIV-infected cells were detected by the rapid and 21-day co-culture methods.

At TCID's of 5 or less detected by the 21 day co-culture assay, the TCID determined by the method of the invention was approximately 50-fold higher. This discrepancy may be due, at least in part, to the presence of cytotoxic/suppressor cells from the patients when assayed by the co-culture method. In preliminary experiments, the addition of anti-CD6 F(ab')$_2$ to the co-culture resulted in a 10-fold or higher TCID. The introduction of a reactive oxygen intermediate generator such as PMA in the method of the invention may induce maximal HIV replication, diminishing the effect of suppressor cells. In addition, the correlation coefficient may also be influenced by the use of 2-fold dilutions of chronically infected cells in the method of the invention versus 10 fold dilutions of patient cells in the 21 day co-culture.

The rapid HIV culture intentionally biases against amplification of the HIV by the short duration of culture. Therefore, the amount of p24 produced by cells cultured in the rapid assay is smaller than the qualitative co-culture assay. In contrast, the design of the qualitative co-culture assay is to amplify HIV by multiple cycles of infection of mitogen stimulated donor cells that results in very high levels of p24 antigen. Although the amount of p24 detected by the rapid culture in some cases is low, this amount is similar to that produced by chronically HIV infected cell lines. Some advantages of the rapid HIV culture method of the invention over the standard co-culture are its ability to overcome variability of cell susceptibility from different donors to HIV-1 infection and possibly higher sensitivity by the culture of $10^7$ cells compared to $2\times10^6$ cells used for the standard quantitative co-culture.

As shown in Table 2 below, the overall sensitivity of the method of the invention in HIV seropositive persons is 87%, and the specificity in HIV seronegative low risk persons is 100%. Excluding the HIV seronegative patient with Guillain-Barré syndrome from the analysis, the positive predictive value of the method of the invention is 100% (20 of 20) and the negative predictive value is 78% (11 of 14).

TABLE 2

Sensitivity and Specificity of Rapid HIV Culture[f]

| Rapid HIV Culture: | HIV Status | | |
|---|---|---|---|
| | HIV Seropositive | HIV Seronegative | Total |
| Positive | 20 | 0 | 20 |
| Negative | 3 | 11 | 14 |
| Total | 23 | 11 | 34 |

Sensitivity: 87% (20 of 23), specificity: 100% (11 of 11), positive predictive value: 100% (20 of 20), and negative predictive value, 79% (11 of 14)
[f]HIV serology was determined by The New York Hospital Clinical Laboratory. Of the 23 HIV seropositive patients, cells were available to perform the 21 day viral co-culture in 19, all of whom were co-culture positive.

The method of the invention is comparable in sensitivity and specificity to HIV culture studies published, for example, in Alimenti, et al., *Diagnosis of Vertical Human Immunodeficiency Virus Type 1 Infection By Whole Blood Culture*, J. Infect. Dis., v. 166, pp. 1146–48 (1992), Castro, et al., *Optimal Conditions for Recovery of the Human Immunodeficiency Virus From Peripheral Blood Mononuclear Cells*, J. Clin. Microbiol., v. 26, pp. 2371–76 (1988), Jackson, et al., *Rapid and Sensitive Viral Culture Method for Human Immunodeficiency Virus Type 1*, J. Clin. Microbiol., v. 26, pp. 1416–18 (1988), Schochetman, et al., *Serodiagnosis of Infection With the AIDS Virus and Other Human Retroviruses*, Annu. Rev. Microbiol., v. 43, pp. 629–59 (1989), and Schupbach, et al., *False-Positive HIV-1 Virus Culture Using Whole Blood*, AIDS, v. 6, pp. 1545–46 (1992). These studies have reported sensitivities of 10% to 100%, depending in part on culture conditions and the stage of HIV disease, with AIDS patients most likely to yield a positive viral culture. The sensitivity of the method of the invention may be improved by the use of additional cytokines such as TNF-α.

Specifically, the method of the invention is comparable in sensitivity to polymerase chain reaction using DNA from cells lysed directly, as described in Bylund, et al., *Review of Testing For Human Immunodeficiency Virus*, Laboratory Immunology II. Clin. Lab. Med., v. 12, pp. 305–333 (1992), and Jackson, et al., *Human Immunodeficiency Virus Type 1 Detected in All Seropositive Symptomatic and Asymptomatic Individuals*, J. Clin. Microbiol., v. 28, pp. 16–19 (1989). The sensitivity of PCR can be less than 100% if the frequency of infected PBMCs is less than 1 per 250,000, or if contamination with hemoglobin interferes with the PCR reaction, as described in Ou, et al., *Rapid and Quantitative Detection of Enzymatically Amplified HIV-1 DNA Using Chemiluminescent Oligonucleotide Probes*, AIDS Res. Hu. Retrovir., v. 6, pp. 1323–1329, and Wages, et al., *Clinical Performance of a Polymerase Chain Reaction Testing Algorithm for Diagnosis of HIV-1 Infection in Peripheral Blood Mononuclear Cells*, v. 33, pp. 58–63 (1991).

Another advantage of the rapid-culture method of the invention is the ability to monitor the viral load in relation to the stage of HIV disease and response to antiretroviral therapy. Although levels of HIV mRNA and DNA also provide information on the viral load, the method of the invention provides information on the replication competence of cells infected with HIV. Differences in viral quantitation by DNA PCR and viral culture have been obvserved and attributed to measurements of proviral copies of HIV and replication-competent virions, as described in Bernard, et al., *Cell Associated HIV Detection and Quantitation by Culture and Gag Gene Polymerase Chain Reaction Amplification*, Conf. Adv. AIDS Vaccine Dev., 6th NCVDG Meet (1993); and Bieniasz, et al., *Variable Relationship Between Proviral DNA Load and Infectious Virus Titer in the Peripheral Blood Mononuclear Cells of HIV-1 Infected Individuals*, AIDS, v. 7, pp. 803–806 (1993). Detection of large numbers of HIV mRNA copies by reverse transcription-PCR has been reported to correlate with disease progression, as described in Saksela, et al., *Human Immunodeficiency Virus Type 1 mRNA Expression in Peripheral Load Cells Predicts Disease Progression Independently of the Numbers of CD4+Lymphocytes*, Proc. Natl. Acad. Sci. U.S.A., v. 91, pp. 1104–1108 (1994). The use of newer antiretroviral agents, such as protease inhibitors, that act on posttranscriptional events may make the quantitation of cell-associated mRNA less likely to correlate with production of infectious virions. The ability of the method of the invention to detect intracellular and released viruses obviates this limitation. It is likely that the quantitation of the virus load in plasma by competitive PCR and plasma viral culture may be the only assays comparable to the method of the invention as described in Coombs, et al., *Plasma Viremia in Human Immunodeficiency Virus Infection*, N. Engl. J. Med., v. 321, pp. 1626–1631 (1989); Ho, et al., *Quantitation of Human Immunodeficiency Virus Type 1 in the Blood of Infected Persons*, N. Engl. J. Med., v. 321, pp. 1621–1625 (1989); and Piatak, et al., *High Levels of HIV-1 in Plasma During All Stages of Infection Determined by Competitive PCS*, Science, v. 259, pp. 1749–1754 (1993). These assays are limited by either their complexity or their potential for contamination.

The method of the invention is also superior to the detection of serum HIV p24 antigen, in which the rate of positivity is between 4% and 70%, depending on the stage of HIV disease, i.e., 4% to 17% in symptom-free and 42% to 70% in AIDS patients, as described in Coombs, et al., *Plasma Viremia in Human Immunodeficiency Virus Infection*, New Eng. J. Med., v. 321, pp. 1626–31 (1989); Harvey, et al., *Antigen Detection for Human Immunodeficiency Virus*, Clin. Microbial. Rev., v. 2, pp. 241–60 (1989); Holzer, et al., *Frequency of Cells Positive for HIV-1 p24 Antigen Assessed By Flow Cytometry*, AIDS, v. 7 (supp. 2), pp. S3-S5 (1993); and Jackson, et al., *Human Immunodeficiency Virus Type I Detected in All Seropositive Symptomatic and Asymptomatic Individuals*, J. Clin. Microbial., v. 28, pp. 16–19 (1990).

Many of the patients assayed in the method of the invention were receiving anti-retroviral therapy and chemoprophylaxis for opportunistic infections, and five of the 23 HIV seropositive patients had clinical AIDS defining illness. Viral load as defined by TCID per $10^6$ PBMC poorly correlated with the absolute CD4+ T cells. The Pearson correlation coefficient was 0.00 (95% confidence interval, 0.42 to 0.42, not statistically significant).

The rapid HIV assay for seven patients was compared after 1 and 7 days. Of the seven rapid cultures positive at 7 days, two were positive after 1 day of culture. In addition, preliminary experiments in which whole blood was stimulated with PHA for 3 to 7 days resulted in significant cell death. After preliminary trials with various time points, 7 days was chosen as a time point which most probably would (i) result in an acceptable sensitivity, (ii) reduce the number of days needed to perform the culture relative to the standard co-culture method, and (iii) minimize cell death because of the lack of medium replacement.

In order to compare numbers of HIV infected cells defined by the rapid culture method of the invention and the prior 21 day co-culture method, the standard curves prepared as described above for the chronically infected U1 and ACH-2 cell lines were used to determine presumed numbers of HIV infected PBMCs based on the amount of p24 antigen detected in the method of the invention.

Figure 4:
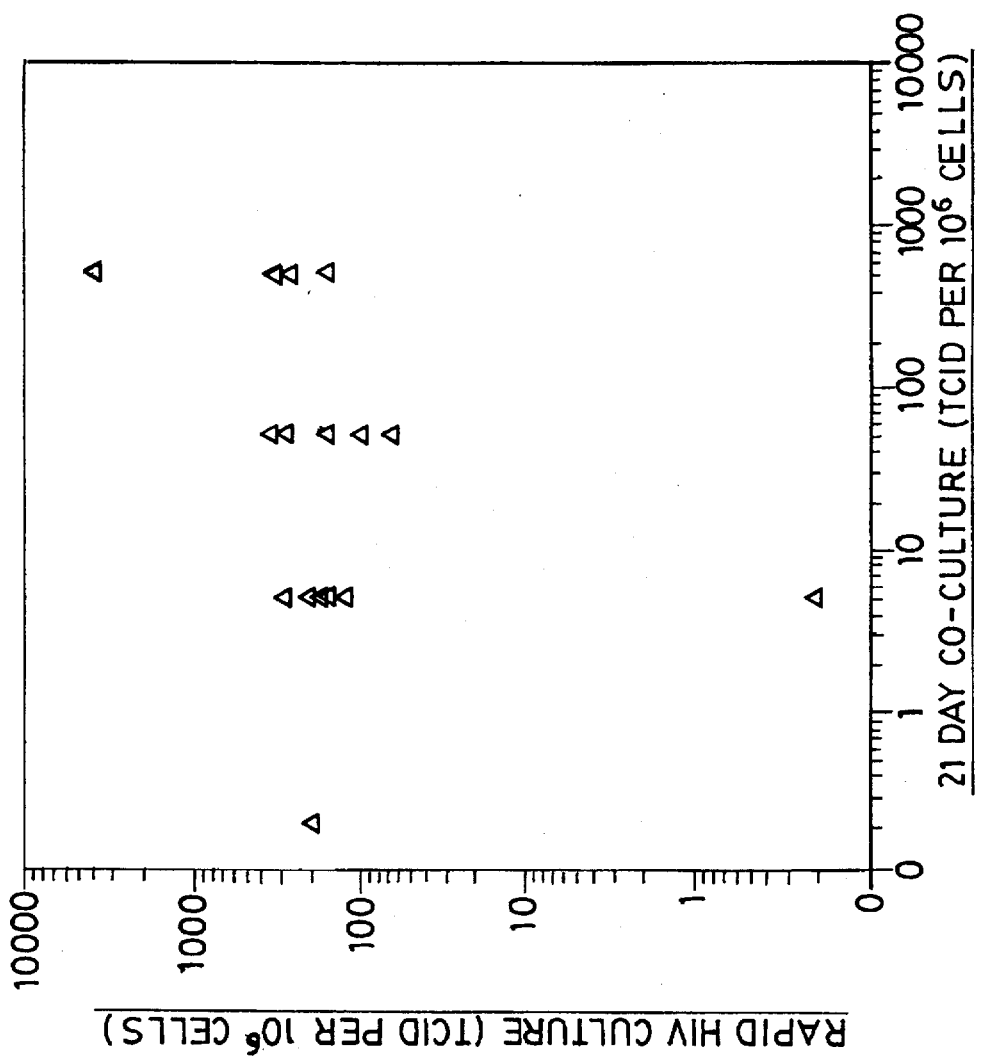
FIG. 4 is a plot of the tissue culture infective dose (TCID) (per $10^6$ PBMC) determined in the method of the invention from the standard curve for the mean of U1 and ACH-2 cells shown in FIG. 1 versus TCID (per $10^6$ PBMC) in the prior 21-day co-culture method.

FIG. 4 illustrates the viral quantitation in TCID per $10^6$ PBMC determined from the amounts of p24 antigen listed in Table 1 using the U1, ACH-2, and mean standard curves shown in FIG. 1. The presumed number of HIV infected cells determined from the ACH-2 standard curve is slightly higher than that determined from the U1 standard curve. However, the standard curve of the mean of U1 and ACH-2 cells yielded a number of HIV infected cells which is comparable to that determined in the 21 day co-culture assay. The Pearson correlation coefficient was 0.5 (95% confidence interval, 0.07 to 0.77, P<0.04).

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for the determination of the approximate number of HIV-1-infected patient cells in a patient sample, wherein said patient cells are subjected to direct stimulation in the absence of co-culture with donor cells, comprising the following steps:

(a) obtaining patient cells from a subject who is or may be infected with the HIV-1 virus and suspending said cells in culture media;

(b) directly stimulating said patient cells to activate expression of any HIV-1 virus present and corresponding p24 antigen production, in the absence of donor cell co-cultivation, through the administration of one or more reactive oxygen intermediate generators;

(c) detecting any p24 antigen production in said patient cells and associated culture supernatants following said stimulating; and (d) comparing the p24 antigen production of step (c) with standard values obtained from a culture comprising HIV-1 chronically infected cell lines of known proviral copy number directly stimulated as in step (b); wherein said comparison results in the approximation of the number of HIV-1-infected patient cells in the sample.

2. A method as claimed in claim 1, wherein said standard values are obtained from a standard curve representing the amount of p24 antigen per number of cells from said HIV-1-infected cell lines.

3. A method as claimed in claim 1, further comprising:
separating said culture media into patient cell and culture supernatant fractions following step (b), wherein said detecting is carried out in each of said patient cell and said culture supernatant fractions.

4. A method as claimed in claim 1, wherein said patient cells are selected from the group consisting of peripheral blood mononuclear cells, bone marrow cells, lymph node cells, and cerebral spinal fluid cells.

5. A method as claimed in claim 4, wherein said patient cells are peripheral blood mononuclear cells.

6. A method as claimed in claim 1, wherein said directly stimulating is carried out under conditions suitable for said p24 antigen production.

7. A method as claimed in claim 1, wherein said directly stimulating is carried out by adding an exogenous oxygen generator to said culture media.

8. A method as claimed in claim 7, wherein said exogenous oxygen generator is selected from the group consisting of glucose, glucose oxidase, hydrogen peroxide, compounds capable of releasing hydrogen peroxide, superoxide, and mixtures thereof.

9. A method as claimed in claim 1, wherein said directly stimulating is carried out by adding one or more phorbol esters capable of inducing intracellular oxygen radical generation and/or activating protein kinase C, or mixtures thereof, to said culture media.

10. A method as claimed in claim 9, wherein said phorbol ester is phorbol-12-myristate-13-acetate.

11. A method as claimed in claim 1, wherein step (a) or step (b) further comprises:
introducing one or more cytokines into said culture media.

12. A method as claimed in claim 11, wherein said cytokines are selected from the group consisting of interleukin-2, tumor necrosis factor-$\alpha$, interleukin-1, interleukin-6 and mixtures thereof.

13. A method as claimed in claim 10, wherein said Phorbol-12-myristate-13-acetate is added to said culture media in an amount of from about 10 to about 50 ng/ml media.

14. A method as claimed in claim 8, wherein said glucose oxidase is added to said culture media in an amount of from about 5 to about 25 U/ml, or said glucose, hydrogen peroxide, compound capable of releasing hydrogen peroxide, superoxide or mixture thereof is added to said culture media in an amount of from about 1 nM to about 100 mM.

15. A method as claimed in claim 11, wherein said cytokine(s) are added to said culture media in an amount of from 1 to 5 ng/ml media.

16. A method as claimed in claim 1, wherein said culture media further comprises one or more additives selected from the group consisting of antibiotics, buffering agents, and nutrient sources.

17. A method as claimed in claim 16, wherein said antibiotics are penicillin, streptomycin, ampicillin, and gentamycin, said buffering agents are HEPES and sodium bicarbonate, and said nutrient sources are fetal bovine serum, synthetic serum, amino acids, growth factors, and mixtures thereof.

18. A method as claimed in claim 1, wherein said directly stimulating is carried out for a period of from about 5 to about 8 days, at a temperature of from about 25° to about 37° C., a humidity of from about 80% to about 98%, and an atmospheric carbon dioxide concentration of from about 3% to about 6%.

19. A method as claimed in claim 18, wherein said period is about 7 days, said temperature is from about 35° to about 37° C., said humidity is from about 90% to about 95%, and said carbon dioxide concentration is about 5%.

20. A method as claimed in claim 1, wherein said patient cells are suspended in said culture media in a concentration of from about $0.5 \times 10^6$ to about $2 \times 10^6$/ml media.

21. A method as claimed in claim 1, wherein said patient cells are suspended in said culture media in a concentration of about $1 \times 10^6$/ml media.

22. A method as claimed in claim 1, wherein said detecting comprises employing a HIV-1 p24 antigen-specific immunoassay.

23. A method as claimed in claim 22, wherein said immunoassay is a p24 antigen capture assay.

24. A method for the determination of the approximate number of HIV-1-infected patient cells in a patient sample, wherein said patient cells are subjected to direct stimulation in the absence of co-culture with donor cells, comprising the following steps:

(a) obtaining peripheral blood mononuclear cells from a subject who is or may be infected with the HIV-1 virus and suspending said cells in culture media in a concentration of from about 0.5 to about $2 \times 10^6$/ml medium;

(b) directly stimulating said peripheral blood mononuclear cells to activate expression of any HIV-1 virus present and corresponding p24 antigen production, in the absence of donor cell co-cultivation, by adding to said culture media phorbol-12-myristate-13-acetate in an amount of from 10 to 50 ng/ml media and interleukin-2 in an amount of from 6 to 20 units/ml media and incubating the resulting mixture for a period of from about 5 to about 7 days, at a temperature of from about 35° to about 37° C., a humidity of from about 90% to about 95%, and an atmospheric carbon dioxide concentration of from about 4% to about 5%;

(c) separating the culture media following step (b) into cell and culture supernatant fractions and detecting any p24 antigen production in each of said cell and culture supernatant fractions; and (d) comparing the p24 antigen production of step (c) with standard values obtained from a culture comprising HIV-1 chronically infected cell lines of known proviral copy number directly stimulated as in step (b), wherein said standard values are obtained from a standard curve representing the amount of p24 antigen per number of cells from said HIV-1-infected cell lines;

wherein said comparison results in the approximation of the number of HIV-1-infected patient cells in the sample.

* * * * *